US010578702B2

(12) United States Patent
Kim

(10) Patent No.: US 10,578,702 B2
(45) Date of Patent: Mar. 3, 2020

(54) IMAGING PHANTOM AND SYSTEMS AND METHODS OF USING SAME

(71) Applicants: Southern Research Institute, Birmingham, AL (US); The UAB Research Foundation, Birmingham, AL (US)

(72) Inventor: Harrison Kim, Birmingham, AL (US)

(73) Assignees: UAB Research Foundation, Birmingham, AL (US); Southern Research Institute, Birmingham, AL (US)

( * ) Notice: Subject to any disclaimer, the term of this patent is extended or adjusted under 35 U.S.C. 154(b) by 5 days.

(21) Appl. No.: 15/764,560

(22) PCT Filed: Sep. 30, 2016

(86) PCT No.: PCT/US2016/054822
§ 371 (c)(1),
(2) Date: Mar. 29, 2018

(87) PCT Pub. No.: WO2017/059269
PCT Pub. Date: Apr. 6, 2017

(65) Prior Publication Data
US 2018/0275240 A1    Sep. 27, 2018

Related U.S. Application Data

(60) Provisional application No. 62/236,323, filed on Oct. 2, 2015.

(51) Int. Cl.
G01R 33/58    (2006.01)
A61K 49/06    (2006.01)
(52) U.S. Cl.
CPC ............ *G01R 33/583* (2013.01); *A61K 49/06* (2013.01)

(58) Field of Classification Search
CPC .. G01R 33/583; G01R 33/58; G01R 33/5601; G01R 33/56366; A61K 49/06; G01V 3/14; G06B 23/286; G06B 23/303; G06B 23/30
See application file for complete search history.

(56) References Cited

U.S. PATENT DOCUMENTS 4,625,168 A    11/1986 Meyer et al.
4,719,406 A    1/1988 Schaefer et al.
(Continued)

FOREIGN PATENT DOCUMENTS

DE    102009021099 B4    4/2011
WO    WO-2014/140547 A1    9/2014
WO    WO-2017/059269 A1    4/2017

OTHER PUBLICATIONS

International Search Report and Written Opinion were dated Dec. 13, 2016 by the International Searching Authority for Application No. PCT/US2016/054822, filed Sep. 30, 2016, and published as WO 2017/059269 on Apr. 6, 2017 (Applicant—Southern Research Institute) (15 pages).

(Continued)

*Primary Examiner* — Gregory H Curran
(74) *Attorney, Agent, or Firm* — Ballard Spahr LLP

(57) ABSTRACT

An imaging phantom having a housing and a dynamic perfusion assembly positioned within the housing. The dynamic perfusion assembly permits the flow of at least one contrast agent into a non-contrast solution at a desired rate. The dynamic perfusion assembly includes a first chamber that receives at least one contrast agent and a second chamber that receives a non-contrast solution. The second chamber receives the at least one contrast agent from the first chamber at the desired rate.

17 Claims, 13 Drawing Sheets

(56) References Cited

U.S. PATENT DOCUMENTS

| | | | |
|---|---|---|---|
| 4,888,555 | A | 12/1989 | Vaughan et al. |
| 4,985,906 | A | 1/1991 | Arnold |
| 5,362,622 | A | 11/1994 | O'Dell et al. |
| 6,364,520 | B1 | 4/2002 | Steele |
| 7,368,912 | B2 | 5/2008 | Kreibich |
| 7,439,493 | B2 | 10/2008 | Teppaz et al. |
| 7,612,560 | B2 | 11/2009 | Wiggins |
| 7,642,775 | B2 | 1/2010 | Katscher et al. |
| 8,188,416 | B2 | 5/2012 | Borenstein et al. |
| 8,339,138 | B2 | 12/2012 | Parker et al. |
| 8,553,964 | B2 | 10/2013 | Chefd'hotel et al. |
| 8,563,919 | B2 | 10/2013 | Coolens et al. |
| 8,804,904 | B2 | 8/2014 | Hirschenbain et al. |
| 8,846,034 | B2 | 9/2014 | Jiang et al. |
| 9,013,182 | B2 | 4/2015 | Jena et al. |
| 2003/0086535 | A1* | 5/2003 | Teppaz .................. A61B 6/583 378/207 |
| 2008/0012561 | A1 | 1/2008 | Ashton |
| 2009/0316972 | A1 | 12/2009 | Borenstein et al. |
| 2011/0293074 | A1 | 12/2011 | Coolens et al. |
| 2013/0200900 | A1 | 8/2013 | Buurman et al. |
| 2014/0227177 | A1 | 8/2014 | Nijsen et al. |
| 2015/0085993 | A1 | 3/2015 | Scheib |
| 2015/0091562 | A1 | 4/2015 | Rivet-Sabourin et al. |
| 2015/0141804 | A1 | 5/2015 | Rooney et al. |
| 2015/0323639 | A1 | 11/2015 | Boss |

OTHER PUBLICATIONS

International Preliminary Report on Patentability was dated Apr. 3, 2018 by the International Searching Authority for Application No. PCT/US2016/054822, filed Sep. 30, 2016, and published as WO 2017/059269 on Apr. 6, 2017 (Applicant—Southern Research Institute) (14 pages).

European Search report was dated May 13, 2019 by the European Patent Office for EP Application No. 16852724.0, filed on Sep. 30, 2016 and published as EP 3356863 A1 on Aug. 8, 2018 (Applicant—Southern Research Institute) (7 Pages).

Bosca, et al., "RSNA Quantitative Imaging Biomarker Alliance (QIBA) DCE-MRI Phantom: Goal, Design, and Initial Results", Radiological Society of North America 2012 Scientific Assembly and Annual Meeting, (2012).

Driscoll et al., "Development of a dynamic flow imaging phantom for dynamic contrast-enhanced CT", Medical Physics (2011), 38(8):4866-80.

Hariharan, et al., "Use of computational fluid dynamics in the design of dynamic contrast enhanced", Phys Med Biol. Sep. 21, 2013;58(18):6369-91 (2013).

Otton et al., A direct comparison of the sensitivity of CT and MR cardiac perfusion using a myocardial perfusion phantom, Journal of Cardiovascular Computed Tomography 7, 117-124 (2013).

Pang, Design and Characterization of a Multi-Modality Phantom for Contrast Enhanced Ultrasound and Magnetic Resonance Imaging, Master of Science Thesis Graduate Department of Medical Biophysics University of Toronto (2011); available at: https://tspace.library.utoronto.ca/handle/1807/29597; downloaded on Aug. 28, 2015.

Rajan et al., "A dialyzer-based flow system validating dynamic contrast enhanced MR image acquisition", Magnetic Resonance in Medicine (2014), 72(1):41-48.

Ussing Chamber System Brochure, Guide to Ussing Chamber Systems, Brochure, www.warneronline.com.

* cited by examiner

PHANTOM (TOP VIEW)

PHANTOM (SIDE VIEW)

PHANTOM SCHEMATIC

IMAGING PHANTOM AND SYSTEMS AND METHODS OF USING SAME

CROSS-REFERENCE TO RELATED APPLICATION

This application claims priority to and the benefit of the filing date of U.S. Provisional Patent Application No. 62/236,323, filed Oct. 2, 2015, which is incorporated herein by reference in its entirety.

STATEMENT OF GOVERNMENT SUPPORT

The present application is a national phase filing under 35 U.S.C. § 371 of International Application No. PCT/US2016/054822, filed on Sep. 30, 2016, which claims priority to U.S. provisional application Ser. No. 62/236,323, filed on Oct. 2, 2015, the content of which is incorporated herein by reference in its entirety.

FIELD

Disclosed herein is an imaging phantom that can be used to normalize data obtained using varying protocols for a particular imaging device.

BACKGROUND

DCE-MRI (dynamic contrast enhanced magnetic resonance imaging) is a physiologic MRI technique that quantifies perfusion (or permeability) in a target tissue. However, due to the variability in quantitative perfusion parameters across MR imaging platforms, the use of DCE-MRI in multi-center trials has been very limited. Imaging phantoms simulating characteristics of the human body have been developed to allow for system calibration or pharmacokinetic model studies. However, those existing phantoms are too bulky to be imaged concurrently with a test subject, making it impossible to compensate for MR signal fluctuation (during image acquisition) or the variation of quantitated values between acquisitions. Additionally, the calibrated data that is obtained using these existing phantoms is not directly applicable to images acquired with different protocols, even if the same type of machine is used. Third, the high cost of such phantoms restricts the potential of routine clinical use.

Thus, there is a need for an imaging phantom that addresses one or more of the deficiencies of existing imaging phantoms. For example, there is a need for an imaging phantom that can compensate for variations between image acquisitions and/or allow for normalization of data obtained using varying imaging protocols.

SUMMARY

Described herein, in various aspects, is an imaging phantom. The imaging phantom can have a housing and a dynamic perfusion assembly positioned within the housing. In operation, the dynamic perfusion assembly can permit the flow of at least one contrast agent into a non-contrast solution at a desired rate. The dynamic perfusion assembly can have a first chamber configured to receive at least one contrast agent and a second chamber configured to receive a non-contrast solution. The second chamber can be configured to receive the at least one contrast agent from the first chamber at the desired rate. Optionally, the first chamber of the dynamic perfusion assembly can be configured to receive at least one MRI contrast agent, and the second chamber can be configured to receive the at least one MRI contrast agent from the first chamber at the desired rate. In use, the dynamic perfusion assembly can be configured to maintain a substantially constant temperature within the first and second chambers. Optionally, the imaging phantom can also include a static chamber positioned within the housing. The static chamber can be configured to receive a liquid mixture of a non-contrast solution and at least one contrast agent. The static chamber can be configured to maintain a concentration of the at least one contrast agent within the liquid mixture. Systems and methods of using the disclosed imaging phantom are also described.

DETAILED DESCRIPTION

Figure 1A:
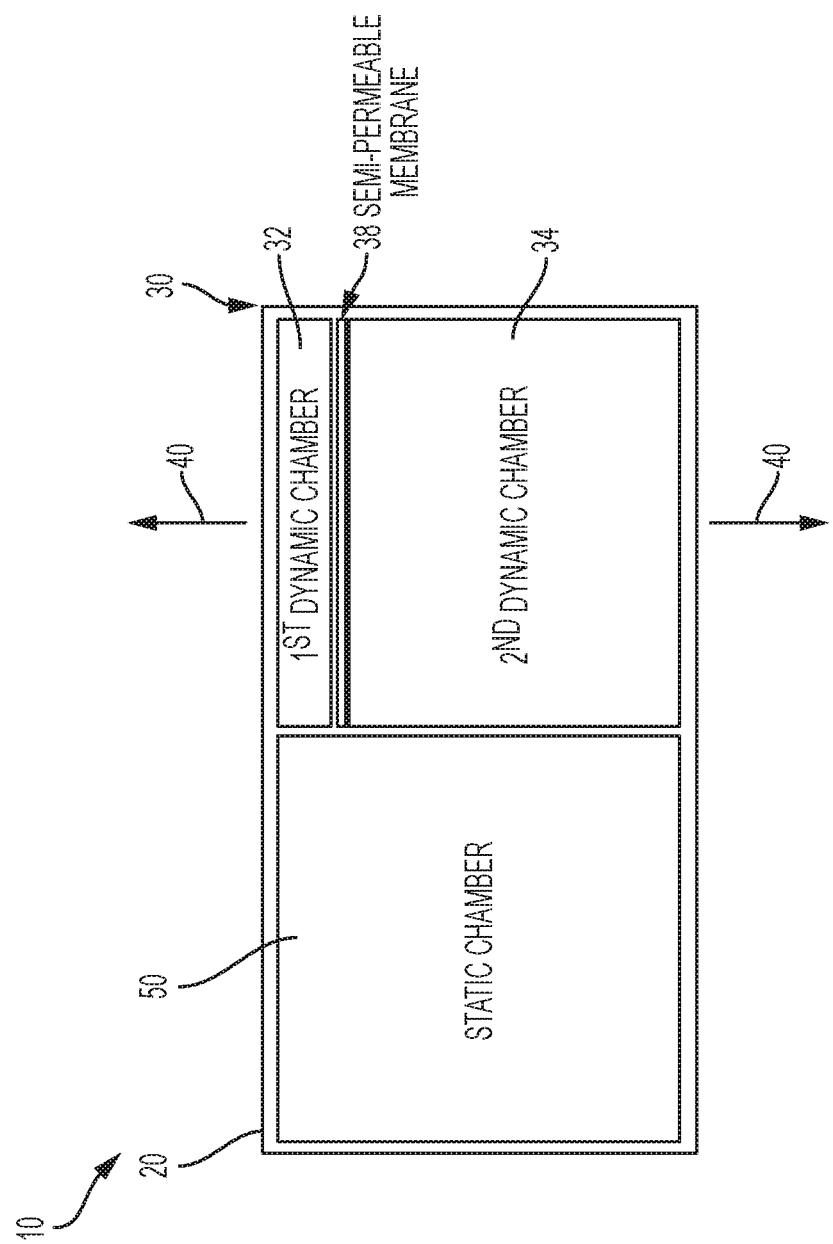
FIG. 1A is a schematic diagram of an exemplary imaging phantom as disclosed herein.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a", "an", and "the" include plural referents unless the context clearly dictates otherwise. For example, use of the term "a chamber" can refer to one or more of such chambers unless the context indicates otherwise.

All technical and scientific terms used herein have the same meaning as commonly understood to one of ordinary skill in the art to which this invention belongs unless clearly indicated otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

Disclosed herein with reference to FIGS. 1A-9B is an imaging phantom 10. In various aspects, the imaging phantom 10 can comprise a housing 20 and a dynamic perfusion assembly 30 positioned within the housing. In operation, the dynamic perfusion assembly 30 can be configured to permit the flow of at least one contrast agent into a non-contrast solution at a desired rate. In exemplary aspects, the desired rate can be a substantially constant rate during an initial perfusion period, which can correspond to a time of less than or equal to 10 minutes after injection of contrast agent, less than or equal to 9 minutes after injection of contrast agent, less than or equal to 8 minutes after injection of contrast agent, less than or equal to 7 minutes after injection of contrast agent, less than or equal to 6 minutes after injection of contrast agent, less than or equal to 5 minutes after injection of contrast agent, less than or equal to 4 minutes after injection of contrast agent, less than or equal to 3 minutes after injection of contrast agent, less than or equal to 2 minutes after injection of contrast agent, or less than or equal to 1 minute after injection of contrast agent. In exemplary aspects, it is contemplated that a substantially constant rate can be a constant rate. In further exemplary aspects, it is contemplated that a substantially constant rate can deviate (upwardly or downwardly) from the desired rate during a portion of the contrast agent flow by up to 25 percent, up to 20 percent, up to 15 percent, up to 10 percent, or up to 5 percent.

In exemplary aspects, and with reference to FIGS. 1A-5C and 8A, the dynamic perfusion assembly 30 can comprise a first chamber 32 configured to receive at least one contrast agent and a second chamber 34 configured to receive a non-contrast solution. In these aspects, the second chamber 34 can be configured to receive the at least one contrast agent from the first chamber 32 at the desired rate. Optionally, and as further disclosed herein, the first chamber 32 of the dynamic perfusion assembly 30 can be configured to receive at least one MRI contrast agent, and the second chamber 34 can be configured to receive the at least one MRI contrast agent from the first chamber at the desired rate.

Figure 8A:
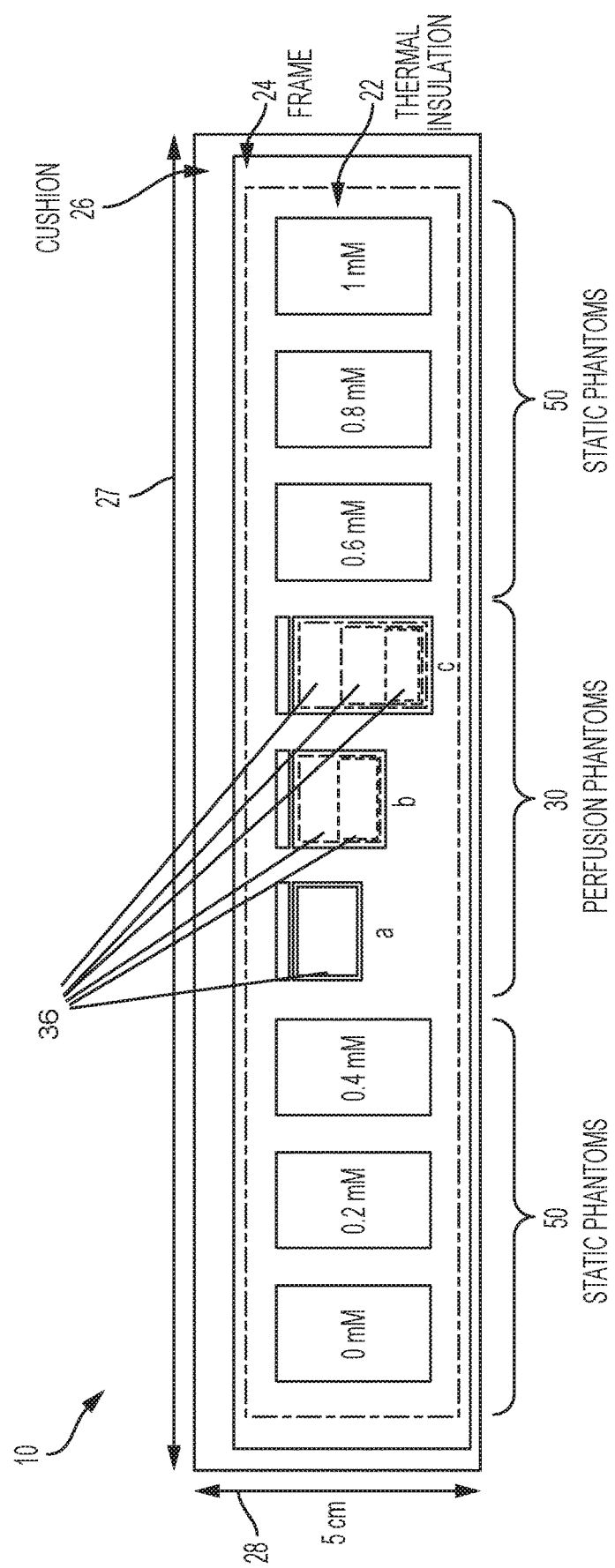
FIG. 8A is a schematic diagram of an exemplary imaging phantom as disclosed herein. As shown, the imaging phantom comprises three perfusion assemblies (a, b, c) having six different ROIs, and six static chambers having different contrast concentrations (0-1 mM).

In another aspect, the dynamic perfusion assembly 30 can be configured to maintain a substantially constant (e.g., a constant) temperature within the first and second chambers 32, 34. In this aspect, it is contemplated that portions of the dynamic perfusion assembly 30 and housing 20 that surround the first and second chambers 32, 34 can comprise one or more thermally insulating materials that define a thermal insulation layer 22. Exemplary thermally insulating materials include glass wool, polymers (polystyrene, polyurethane, melamine, etc), cellulose, cotton, wool, and other insulating materials known in the art. In exemplary aspects, the thermally insulating materials can be configured to permit a selected minimal temperature variation within an hour. Optionally, in these aspects, the selected minimal temperature variation can range from about 0.3 degrees Celsius to about 1 degree Celsius within an hour. Optionally, in exemplary aspects and as shown in FIG. 8A, it is contemplated that at least a portion of the thermal insulation layer 22 can be surrounded by (and, optionally, supported by) a frame 24, which can optionally comprise a plastic or ceramic material. In further exemplary aspects, at least a portion of the frame 24 can optionally be surrounded by a cushion layer 26. In these aspects, it is contemplated that the cushion layer can comprise a foam material, a fiber material, or other resilient material known in the art. It is contemplated that at least a portion of the phantom 10 can be positioned in contact with a subject during an imaging procedure; thus, the thermal insulation layer 22 can prevent undesired transfer of heat from the patient to the phantom 10, the frame 24 can support the weight of the patient, and the cushion layer 26 can provide comfort to the patient. In use, it is contemplated that the frame 24 and the cushion layer 26 can provide additional thermal insulation. It is contemplated that the phantom 10 can have any desired length 27 or height 28. In one exemplary aspect, it is contemplated that the phantom can have a length 27 ranging from about 3 cm to about 20 cm and a height 28 ranging from about 2 cm to about 10 cm. Optionally, in this aspect, the length 27 of the phantom 10 can be greater than the height 28 of the phantom.

Figure 5A:
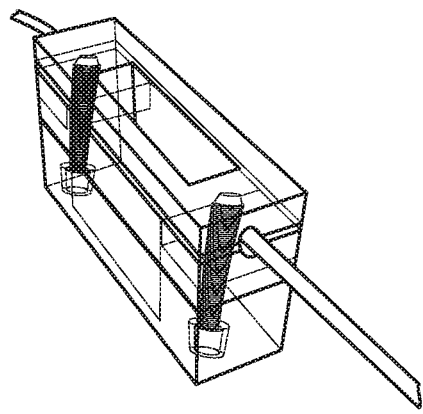
FIGS. 5A-5B are top perspective and side views of an exemplary imaging phantom as disclosed herein.
Figure 5B:
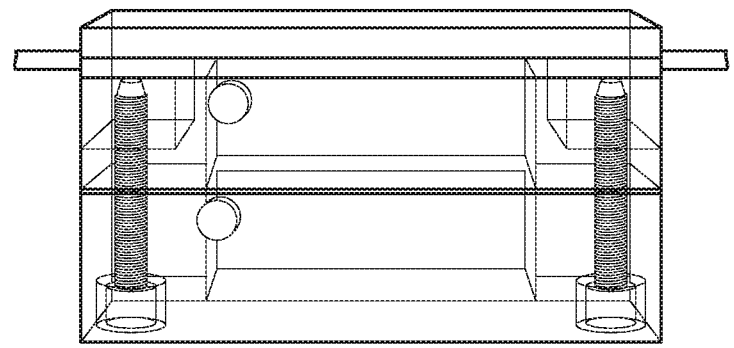
Figure 5C:
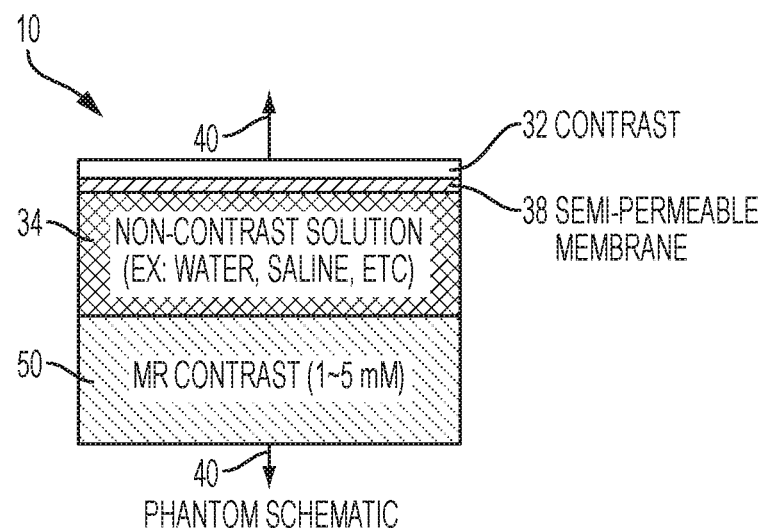
FIG. 5C is a schematic diagram showing the configuration of the imaging phantom of FIGS. 5A-5B. As shown, the phantom can comprise three chambers, with the top chamber (1-mm thick slit) being empty, the middle chamber being filled with non-contrast solution (water, saline, etc), and the bottom chamber being filled with the same type of solution mixed with MR contrast (1~5 mM). As further disclosed herein the top and middle chambers can be separated by a semi-permeable membrane, and the bottom chamber can serve as a reference.

In further exemplary aspects, and with reference to FIGS. 1 and 5C, the dynamic perfusion assembly 30 can further comprise a semi-permeable membrane 38 positioned between and in fluid communication with the first chamber 32 and the second chamber 34. Optionally, in these aspects, the first and second chambers 32, 34 can be spaced apart relative to a perfusion axis 40. It is contemplated that the semi-permeable membrane 38 can have at least a portion that is substantially planar and oriented substantially perpendicularly to the perfusion axis 40. It is further contemplated that the entire semi-permeable membrane 38 can be substantially planar and oriented substantially perpendicularly to the perfusion axis 40. In operation, it is contemplated that the substantially planar and perpendicular orientation of the semi-permeable membrane 38 can be configured to promote consistent transport of contrast agent over all areas of the membrane. Optionally, it is contemplated that the housing 20 can define a ledge portion 29 that is configured to support the semi-permeable membrane 38 in a desired orientation (e.g., a perpendicular orientation) relative to the perfusion axis 40. Exemplary semi-permeable membranes 38 include dialysis membranes as are known in the art, which can optionally comprise regenerated cellulose, cellulose esters, and/or other cellulose-based materials.

In still further exemplary aspects, and with reference to FIGS. 1B-4B, the imaging phantom 10 can further comprise an insert 42 that is secured between the first and second chambers 32, 34 of the dynamic perfusion assembly 30. In these aspects, the insert 42 can be configured to support the semi-permeable membrane 38 in a substantially perpendicular orientation relative to the perfusion axis 40. However, it is contemplated that other orientations of the semi-permeable membrane 38 can be used. Optionally, the insert 42 can be configured to rest against a ledge portion 29 of the housing 20 as depicted in FIGS. 2A, 3A, and 4A. In further aspects, the insert 42 can be configured to mechanically support the semi-permeable membrane 38, while not impeding the fluid communication between the first and second chambers 32, 34. In these aspects, it is contemplated that the insert 42 can comprise a plurality of struts 44 that define a plurality of voids 46 that permit fluid communication between the first and second chambers 32, 34. It is further contemplated that the ratio of the area of the voids 46 to the area of the struts 44 can be maximized to permit suitable fluid communication between the first and second chambers 32, 34. Optionally, the plurality of struts 44 can form a grid pattern as shown in FIGS. 2A, 3A, and 4A. It is further contemplated that by maintaining the substantially planar and perpendicular orientation of the semi-permeable membrane 38, the insert 42 can be configured to ensure that the volume in the first and second chambers is maintained. When the membrane is not flat, it can either sag or float. If the membrane sags, then the total contrast amount in the first chamber can be increased, increasing the likelihood of creating bubbles at the edges of the first chamber. If the membrane floats, then the total contrast amount will be decreased, increasing the possibility of bubbles forming at the float region. So, for data consistency, it is generally desirable to position the membrane as flat as possible. In exemplary aspects, this can be achieved by gluing or otherwise attaching the membrane to the chamber (in case of a disposable device) or using an insert to which the membrane is secured.

Optionally, it is contemplated that the housing 20 can define a slot or other opening (not shown) between the first and second chambers 32, 34 of the dynamic perfusion assembly 30. It is further contemplated that the slot or other opening can be configured to receive the semi-permeable membrane 38 in the desired orientation. It is still further contemplated that the slot or opening can be selectively accessible through a portion of the housing 20.

Optionally, in exemplary aspects and as shown in FIGS. 2A-4B, the housing 20 can comprise multiple components that are selectively secured together after the semi-permeable membrane 38 is positioned in a desired manner. In these aspects, following securing of the various components of the housing 20, the housing can be configured to support the semi-permeable membrane 38 in the desired position relative to the perfusion axis 40.

In exemplary aspects, the housing 20 can define an inlet port 21 and an outlet port 23 that are positioned in fluid communication with the first chamber 32 of the dynamic perfusion assembly 30. In these aspects, the inlet port 21 can be configured to receive a contrast agent and deliver the contrast agent to the first chamber 32, whereas the outlet port 23 can be configured to receive non-contrast solution that is displaced from the first chamber during operation of the dynamic perfusion assembly as further disclosed herein. Thus, in use, the semi-permeable membrane 38 is initially exposed to a non-contrast solution in both the first and second chambers 32, 34. As further disclosed herein, the non-contrast solution within chamber 32 exits the first chamber via outlet port 23 and is displaced by air or immiscible fluid entering though inlet port 21. Following the removal of the non-contrast solution, a contrast agent can be supplied to the first chamber 32 through inlet port 21 using conventional methods. This procedure can minimize dilution of the contrast agent within first chamber 32. More particularly, before flowing contrast agent into the first dynamic chamber 32, the semi-permeable membrane 38 can be provided in a hydrated/wet state to ensure proper functioning of the semi-permeable membrane. Optionally, but preferably, prior to perfusion of contrast agent, the fluid within the first and second dynamic chambers 32, 34 can be identical. However, it is contemplated that some differences between the fluids in the first and second dynamic chambers 32, 34 can be tolerated. In use, the first fluid in the first dynamic chamber 32 must be replaced with a second fluid that contains the contrast agent. In order to minimize dilution of the contrast agent and to expose the entire length of the semi-permeable membrane with the same concentration of contrast agent at the same time, a displacement fluid, which can be, for example and without limitation, a gas (air) or an immiscible fluid, can be flowed through the first dynamic chamber and into a flow collector 25 as shown in FIG. 1B. As the displacement fluid flows through the first dynamic chamber 32, the first fluid can be displaced from the first chamber to the flow collector 25. Optionally, it is contemplated that the first chamber 32 can be generally oriented perpendicularly to the perfusion axis 40 such that the displacement fluid can flow in a direction that is perpendicular or substantially perpendicular to the perfusion axis. Optionally, as shown in FIG. 1B, it is further contemplated that the first chamber 32 can have a length that is greater than the length of the second chamber 34. After the first fluid is displaced from the first dynamic chamber 32, a second fluid containing the contrast agent can be flowed through the first dynamic chamber to permit diffusion of the contrast agent as further disclosed herein. In exemplary aspects, it is contemplated that the volume of the flow collector can be equal to or greater than the volume of the first dynamic chamber. As shown in FIG. 1B, it is contemplated that the flow collector 25 can be positioned at an outlet end of the first chamber 32 such that the flow collector can receive fluid after it passes through the first chamber. In further aspects, it is contemplated that the first chamber 32 can have an inlet end that is positioned in communication with a port defined in the housing of the phantom 10. In still further aspects, it is contemplated that the flow collector 25 can be selectively accessible from the exterior of the phantom 10. In use, it is contemplated that any conventional means of flowing the first fluid, the displacement fluid, or the second fluid can be used.

Alternatively, in other exemplary aspects, a barrier that inhibits fluid communication between the first and second chamber 32, 34 can initially be positioned between the chambers and then removed (via a slot or other opening or release mechanism, not shown) to establish fluid communication between the chambers.

Figure 1B:
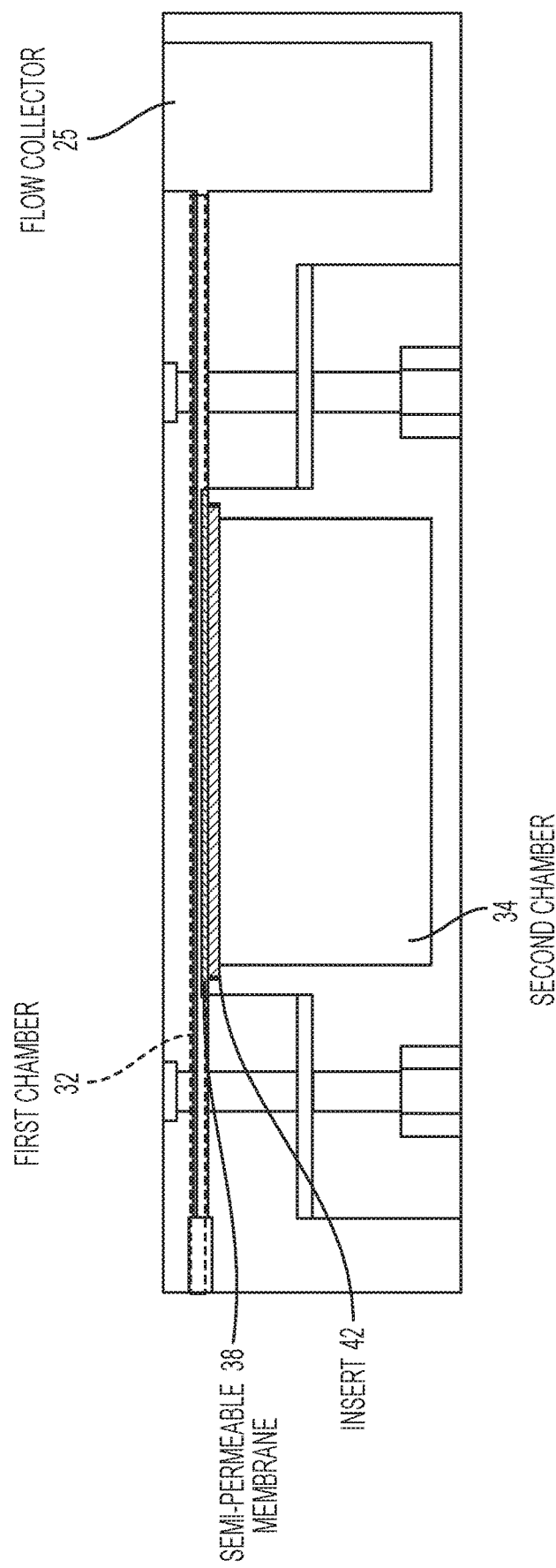
FIG. 1B is a cross-sectional view of an exemplary phantom having an insert and flow collector as disclosed herein.
Figure 2A:
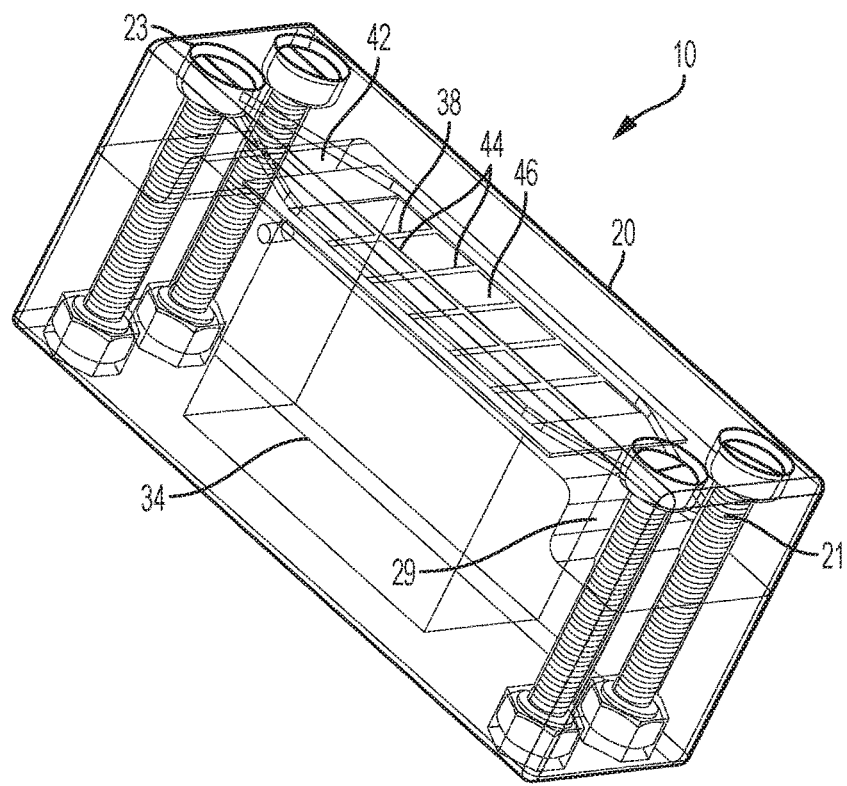
FIGS. 2A-2B are partially transparent perspective and side views of an exemplary imaging phantom as disclosed herein.
Figure 2B:
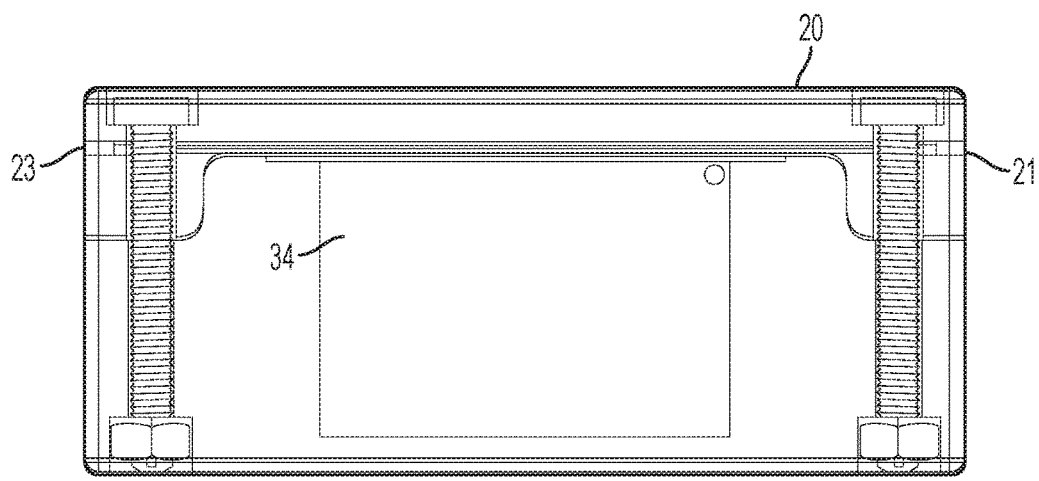
Figure 3A:
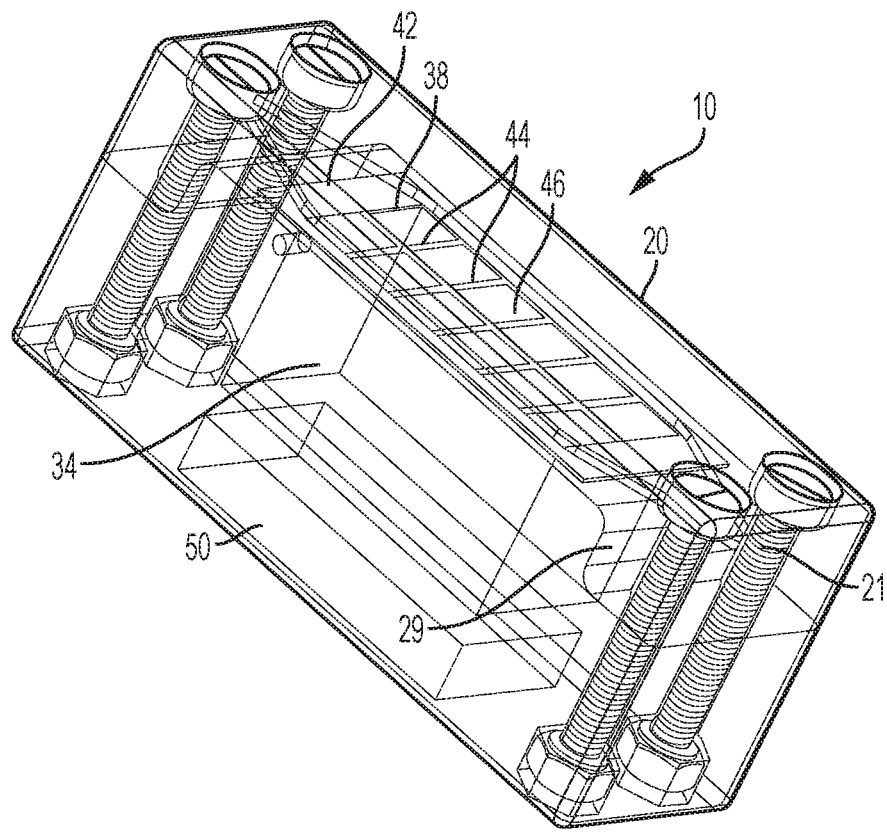
FIGS. 3A-3B are partially transparent perspective and side views of an exemplary imaging phantom as disclosed herein.
Figure 3B:
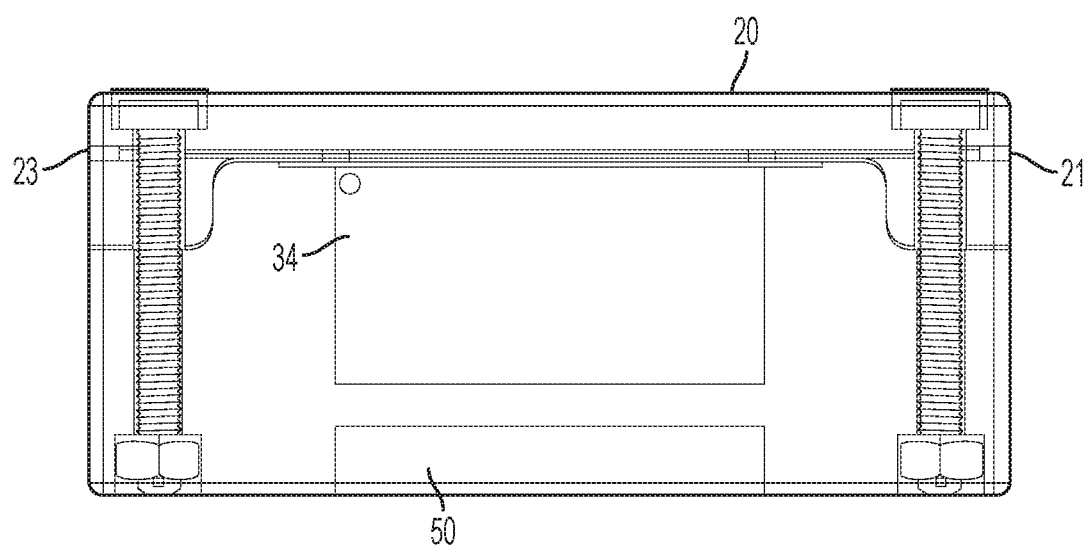
Figure 4A:
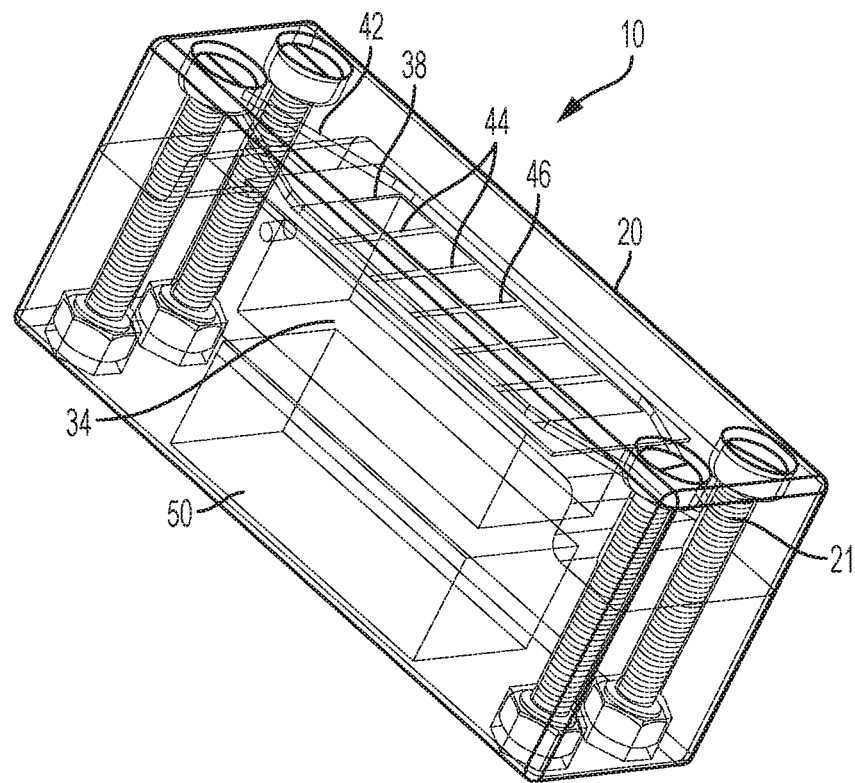
FIGS. 4A-4B are partially transparent perspective and side views of an exemplary imaging phantom as disclosed herein.
Figure 4B:
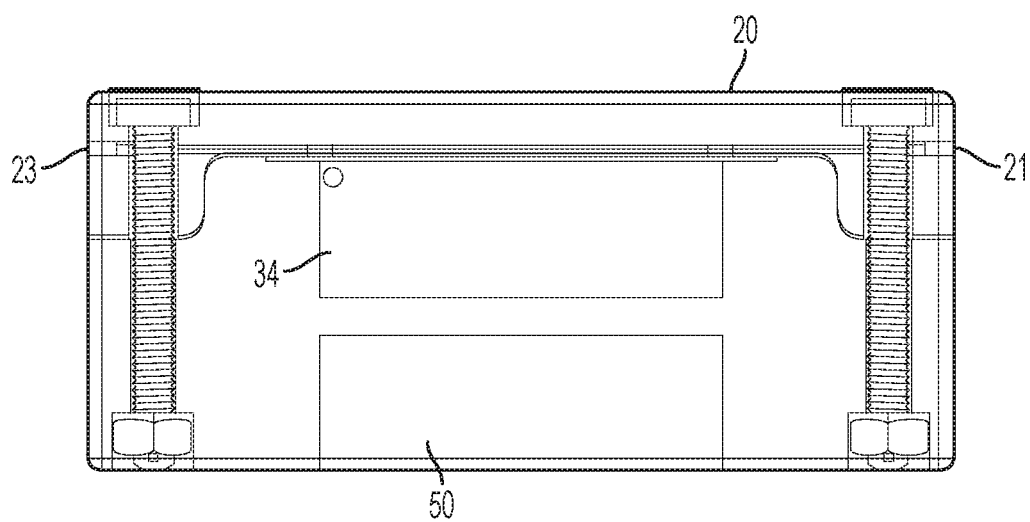

Optionally, in some exemplary aspects, and as shown in FIG. 1A, the imaging phantom 10 can further comprise a static chamber 50 positioned within the housing 20. In these aspects, the static chamber 50 can be configured to receive a liquid mixture of a non-contrast solution and at least one contrast agent. It is contemplated that the static chamber 50 can be configured to maintain a concentration of the at least one contrast agent within the liquid mixture. Alternatively, static chamber 50 may be void of solution and instead be used to account for variations in the volume of the second chamber 34 of the dynamic perfusion assembly 30. For example, as a skilled artisan will appreciate, a static chamber 50 can be provided as shown in FIGS. 3A-4B to allow for manufacture of a housing 20 having consistent wall thicknesses despite variations in the volume of the second chamber 34 and to minimize the volume of material required to produce the phantom 10. Optionally, in some aspects and as shown in FIG. 5C, the static chamber 50 can be positioned in substantial alignment with the perfusion axis 40. Alternatively, in other aspects and as shown in FIG. 1, the static chamber 50 is not aligned with (and optionally has a longitudinal axis oriented substantially parallel to) the perfusion axis 40.

In still further exemplary aspects, the first and second chambers 32, 34 of the dynamic perfusion assembly can have respective volumes that are selected depending upon the particular application, the anatomy of interest, or the field of view. Optionally, in some aspects, the first and second chambers 32, 34 of the dynamic perfusion assembly can have respective volumes ranging from about 0.1 mL to about 1.0 mL (optionally, from about 0.3 mL to about 0.7 mL) and from about 1.0 mL to about 25 mL (optionally, from about 2.0 mL to about 20.0 mL or from about 4.0 mL to about 10.0 mL). However, it is contemplated than any desired volume can be used. For example, in some exemplary applications (e.g., when imaging the pancreas), the volume of the second chamber 34 can range from about 15.0 mL to about 25.0 mL or be about 20.0 mL. In further aspects, the volume of the second chamber 34 can have a desired ratio relative to the volume of the first chamber 32. Optionally, the desired ratio can range from about 1:1 to about 150:1. In use, the semi-permeable membrane 38 can be configured to maintain the respective volumes of the first and second chambers 32, 34 of the dynamic perfusion assembly 30.

In exemplary uses, the imaging phantom 10 can be configured for positioning within a bore of an MRI scanner. However, it is contemplated that the imaging phantom 10 can be used with other imaging modalities, including, for example and without limitation, fluoroscopy, computed tomography (CT), or dynamic positron emission tomography (PET). In one aspect, when the imaging phantom 10 is used with an MRI scanner, the first chamber 32 of the dynamic perfusion assembly 30 can be configured to receive at least one MRI contrast agent, and the second chamber 34 can be configured to receive the at least one MRI contrast agent from the first chamber at the desired rate. In another aspect, when the imaging phantom 10 comprises a static chamber 50, the static chamber can be configured to receive a liquid mixture of a non-contrast solution and at least one MRI contrast agent. In this aspect, the static chamber 50 can be configured to maintain a concentration of the at least one MRI contrast agent within the liquid mixture.

In exemplary aspects, and as shown in FIG. 8A, it is contemplated that the imaging phantom 10 can comprise a plurality of dynamic perfusion assemblies 30, with each assembly comprising a first chamber 32, a second chamber 34, and a respective perfusion axis 40 as disclosed herein. In these aspects, it is further contemplated that each dynamic perfusion assembly 30 can further comprise an insert 42 as disclosed herein. In these aspects, it is still further contemplated that the second chamber 34 of at least one dynamic perfusion assembly 30 of the plurality of dynamic perfusion assemblies can have a different volume than the second chamber of at least one other dynamic perfusion assembly. Optionally, in exemplary aspects, the imaging phantom 10 can comprise a plurality of static chambers 50. In these aspects, it is contemplated that at least one static chamber 50 of the plurality of static chambers can contain a different concentration of contrast agent than at least one other static chamber. In still further exemplary aspects, the imaging phantom 10 can comprise a plurality of dynamic perfusion assemblies 30 and a plurality of static chambers 50 as disclosed herein. Optionally, in exemplary aspects, the perfusion axes of the plurality of dynamic perfusion assemblies 30 and the longitudinal axes of the plurality of static chambers can be substantially parallel to one another. Optionally, in further exemplary aspects, it is contemplated that the dynamic perfusion assemblies 30 can be positioned centrally within the phantom 10. In these aspects, it is contemplated that the central positioning of the perfusion assemblies 30 can reduce the likelihood of geometric distortion, which can occur at the edge of the field of view. Optionally, at least a portion of the static chambers 50 can be positioned within the outer edge portions of the phantom 10. In the event one of these outwardly positioned static chambers 50 suffers from geometrical distortion or low signal-to-noise ratio (SNR), it is possible to rely on the other static chambers 50 within the phantom 10.

Figure 6A:
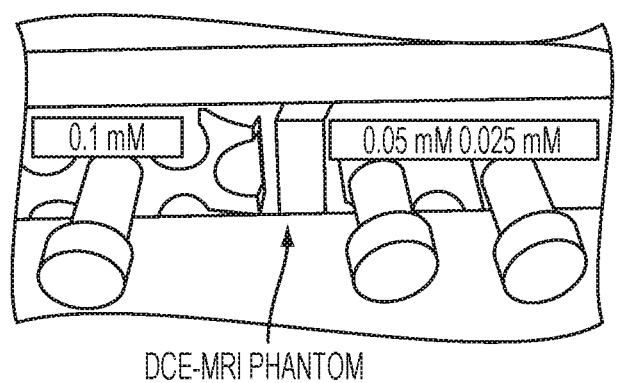
FIG. 6A is a perspective view of a DCE-MRI phantom having three cylindrical phantoms having 0.1, 0.05, and 0.025 mM of gadoteridol.
Figure 6B:
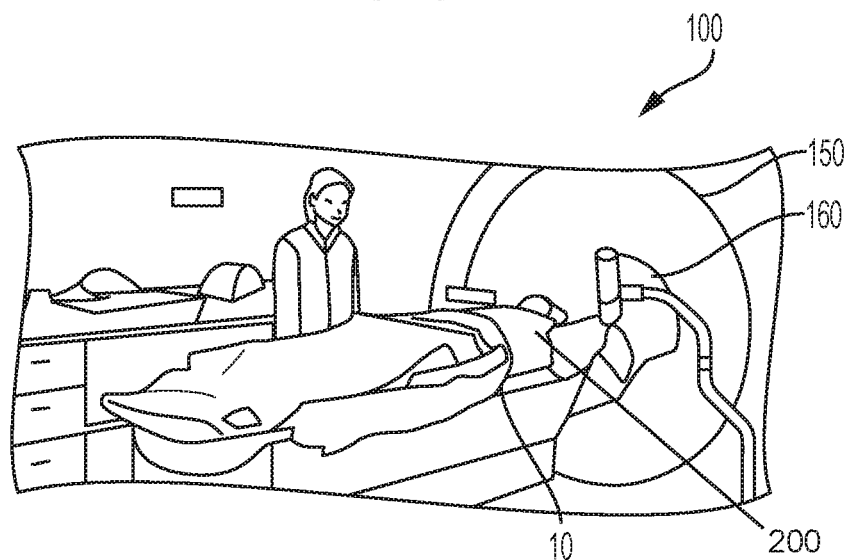
FIG. 6B is a side perspective view of an exemplary imaging system/clinical setup.

In exemplary aspects, and with reference to FIG. 6B, it is contemplated that the imaging phantom 10 can be provided as a component of an imaging system 100. In these aspects, it is contemplated that the imaging system 100 can comprise an imaging device 150 and an imaging phantom 10 as disclosed herein. It is further contemplated that the imaging device 150 can have a bore 160 configured to receive at least a portion of a subject. Optionally, in exemplary aspects, the imaging device 150 can be an MRI scanner as is known in the art. Optionally, in these aspects, the MRI scanner can be an open MRI system or a fMRI system. In other exemplary aspects, it is contemplated that the imaging device 150 can be a fluoroscopy device, a computed tomography (CT)

device (e.g., a dual energy CT device), or a dynamic positron emission tomography (PET) device. In the event a CT device or dynamic PET device is used to image the phantom 10, it is unnecessary to use the semi-permeable membrane 38 as disclosed herein. Instead, contrast can be infused directly into second chamber 34 of the phantom. However, in the event a semi-permeable membrane 38 is used in combination with a CT device or dynamic PET device, it is contemplated that the membrane can be used to control (e.g., slow down) the mixture rate of the contrast and solution. In the event a dynamic PET device is used to image the phantom 10, the size of the second chamber can be enlarged relative to the size of the second chamber used during MRI imaging. In exemplary aspects, when a dynamic PET device is used, the size of the second chamber 34 can be at least 3×3 cm.

In exemplary aspects, an imaging phantom as disclosed herein can be used to perform an imaging method. In these aspects, the imaging method can comprise positioning the imaging phantom within a bore of an imaging device as further disclosed herein. In one aspect, the dynamic perfusion assembly of the imaging phantom permits the flow of at least one contrast agent into a non-contrast solution at a desired rate, which can optionally be a substantially constant rate. In another aspect, the first chamber of the dynamic perfusion assembly receives at least one contrast agent, and the second chamber of the dynamic perfusion assembly receives the at least one contrast agent from the first chamber at the desired rate. In a further aspect, the dynamic perfusion assembly maintains a substantially constant temperature within the first and second chambers. In still further aspects, when the imaging phantom further comprises a static chamber as disclosed herein, the static chamber receives a liquid mixture of a non-contrast solution and at least one contrast agent, and the static chamber maintains a concentration of the at least one contrast agent within the liquid mixture.

In exemplary aspects, the imaging method can comprise positioning the imaging phantom within a bore of an MRI scanner as disclosed herein. In these aspects, the first chamber of the dynamic perfusion assembly receives at least one MRI contrast agent, and the second chamber receives the at least one MRI contrast agent from the first chamber at the desired rate. Optionally, when the imaging phantom comprises a static chamber as disclosed herein, the static chamber receives a liquid mixture of a non-contrast solution and at least one MRI contrast agent, and the static chamber maintains a concentration of the at least one MRI contrast agent within the liquid mixture. In additional aspects, the at least one MRI contrast agent is infused into the first chamber to an initial MRI contrast agent concentration. In further aspects, the method further comprises determining, through a processor, a current MRI contrast agent concentration within the first chamber during operation of the imaging device. In these aspects, the processor can optionally be provided as a component of the imaging device as disclosed herein. Alternatively, the processor can be provided separately from the imaging device (for example, as a component of a computer) but positioned in operative communication with the imaging device. In exemplary aspects, the processor can comprise processing circuitry that is communicatively coupled to at least one memory that stores software, program instructions, data, and the like. In these aspects, the processor can be provided as a component of a computing device, such as, for example and without limitation, a computer, a smartphone, a tablet, a server, a cloud-based computing system, and the like. In further exemplary aspects, the current MRI contrast agent concentration within the first chamber can be determined using the equation:

$$C_{FC}(t) = C_0 - (C_{SC}(t) \times R), \text{ where:}$$

$C_{FC}(t)$ is the current MRI contrast concentration within the first chamber;

$C_0$ is the initial MRI contrast concentration within the first chamber;

$C_{SC}(t)$ is the current MRI contrast concentration within the second chamber; and R is the ratio of the volume of the second chamber to the volume of the first chamber.

In further aspects, the imaging method can comprise operating or activating the imaging device. Optionally, in these aspects, during operation of the imaging device, the imaging phantom and a subject can both be positioned within the bore of the imaging device. Thus, when the imaging device is an MRI scanner, the imaging phantom and a subject can both be positioned within the bore of the MRI scanner.

In operation, it is contemplated that at least one of the following parameters of the phantom can be selectively adjusted or varied: temperature of the image phantom; temperature of respective chambers within the image phantom; volume of the second chambers of the dynamic perfusion assemblies; the porosity and other transport properties of the semi-permeable membrane; the flatness and/or support of the semi-permeable membrane; the concentration and/or amount of contrast agent delivered to the dynamic perfusion assembly; the concentration and/or amount of contrast agent within each static chamber; and the method in which contrast agent is delivered to the image phantom. In exemplary aspects, temperature control can be used to actively control the transport kinetics of the contrast agent moving from the first chamber to the second chamber. In further exemplary aspects, the thermal insulation of the housing can be used to passively control temperature by prolonging the time until thermal equilibrium is achieved.

It is contemplated that the phantoms disclosed herein can be compact enough to be imaged with a test subject and large enough to not suffer from partial volume effect. Therefore, it is contemplated that the phantoms disclosed herein can detect and compensate for hardware- and software-driven errors that may occur during imaging and image processing. It is further contemplated that the phantoms disclosed herein can be inexpensive and simple to use, allowing for easy adoption in routine and global clinical setups. The objective quantification capabilities of the disclosed phantoms can allow for routine use of DCE-MRI in a clinical setting. It is contemplated that DCE-MRI can be used to assess cancer and various other diseases, including cardiac (or cerebral) ischemia, stroke, and neurological diseases.

As further disclosed herein, it is contemplated that the phantom can be used in a variety of anatomical locations and with a variety of different types of machines. In use, calibration and quantification properties can be optimized when the phantom is positioned close to (in the vicinity of) the area of the body to be imaged and the calibration and quantification process is conducted concurrently with imaging of the body.

Figure 9A:
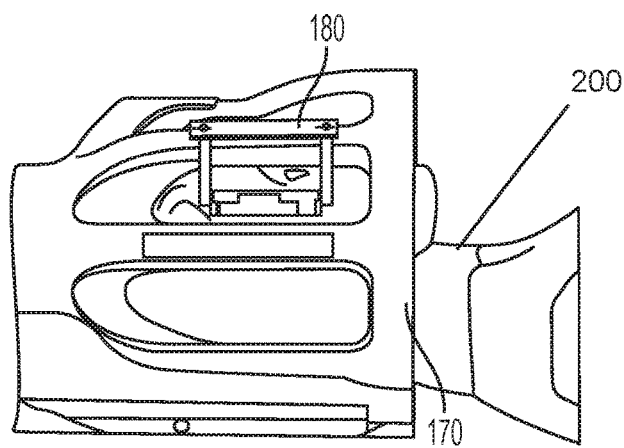
FIGS. 9A and 9B are partial side and end views of an exemplary imaging system including a head coil, a phantom holder assembly, and an imaging phantom as disclosed herein.
Figure 9B:
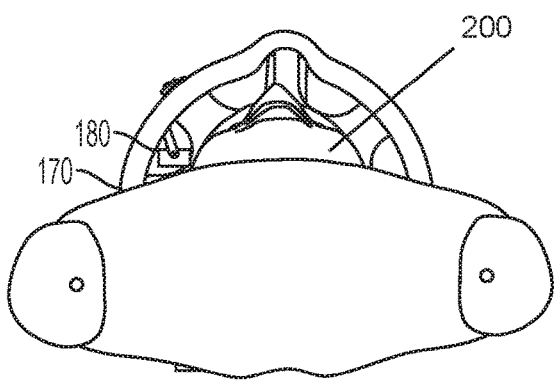

In exemplary aspects, and as further disclosed herein, it is contemplated that the phantom can be supported by a patient support table within the bore of an MR machine. However, it is contemplated that the phantom can interface (and, optionally, be supported by) other components of an MR machine. For example, as shown in FIGS. 9A-9B, it is contemplated that the phantom disclosed herein can be placed next to the body of a subject 200 or within a head coil 170 or body coil that is conventionally used with an MR scanner. As shown, it is contemplated that the coil 170 can comprise a phantom holder assembly 180 that is configured to securely support a phantom in an operative position relative to the coil and the subject 200. In exemplary aspects, the phantom holder assembly can have a base portion that is configured to support the phantom in a desired orientation relative to the subject. Optionally, the base portion can be coupled to the coil by at least one arm (optionally, adjustable arm) that is coupled to the coil by one or more conventional fasteners, brackets, or plates. Optionally, it is contemplated that the base portion can define a receptacle that receives at least a portion of the housing of the phantom disclosed herein.

Because the performance of an MR machine is not uniform throughout the volume of a coil, the region of interest to be scanned will, ideally, be placed at the isocenter (where the central ray of the radiation beam passes). Thus, it is contemplated that positioning of the phantom in proximity to the isocenter can result in improved performance.

EXAMPLES

Example One

An MRI perfusion phantom was produced as disclosed herein. It is contemplated that the MRI perfusion phantom can allow robust reproducibility and comparisons of quantitative perfusion parameters across imaging platforms and analysis software packages. In use, it is contemplated that the disclosed MRI perfusion phantom can present constant perfusion parameters. Since the phantom is small enough to be imaged concurrently in the bore of the MR scanner with a patient, the perfusion parameters in a target tissue can be normalized to those of the phantom, reducing the variability.

The phantom had three chambers as disclosed herein, with the top (1-mm thick slit) being empty, the middle being filled with noncontrast solution, and the bottom being filled with the same type of solution mixed with an MR contrast agent (1~5 mM). The top and middle chambers were separated by a semi-permeable membrane. This feature created a constant model for tissue MR contrast change quantitation over time. MR contrast was infused to the top chamber, and diffused to the middle chamber over time. During an initial perfusion period of about 5 minutes (after injection), the diffusion rate was substantially constant. Since the contrast concentration in the bottom chamber was constant during image acquisition, it can serve as a reference for MR signal fluctuation detection.

In use, the MRI perfusion phantom was imaged concurrently in the bore of an MR scanner with a patient, so that the perfusion parameters in a target tissue could be normalized and quantified in reference to the values observed in the phantom.

Figure 5D:
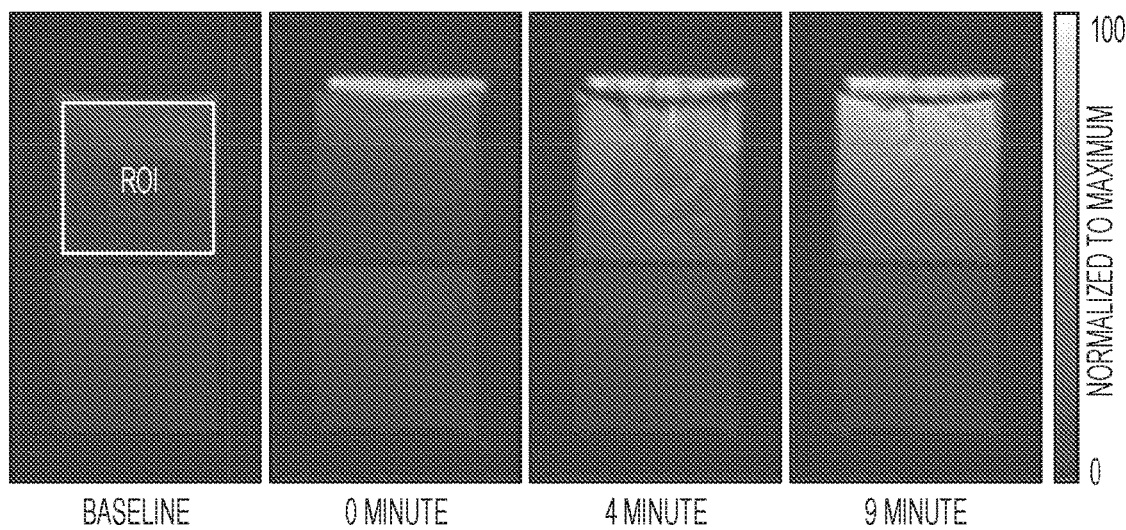
FIG. 5D includes representative DCE-MR images of the phantom at a 9.4 small-animal MR scanner with temporal resolution of 12.8 sec before (baseline) and at 0, 4 and 8.5 minutes after contrast (gadoteridol, 25 mM) infusion.
Figure 5E:
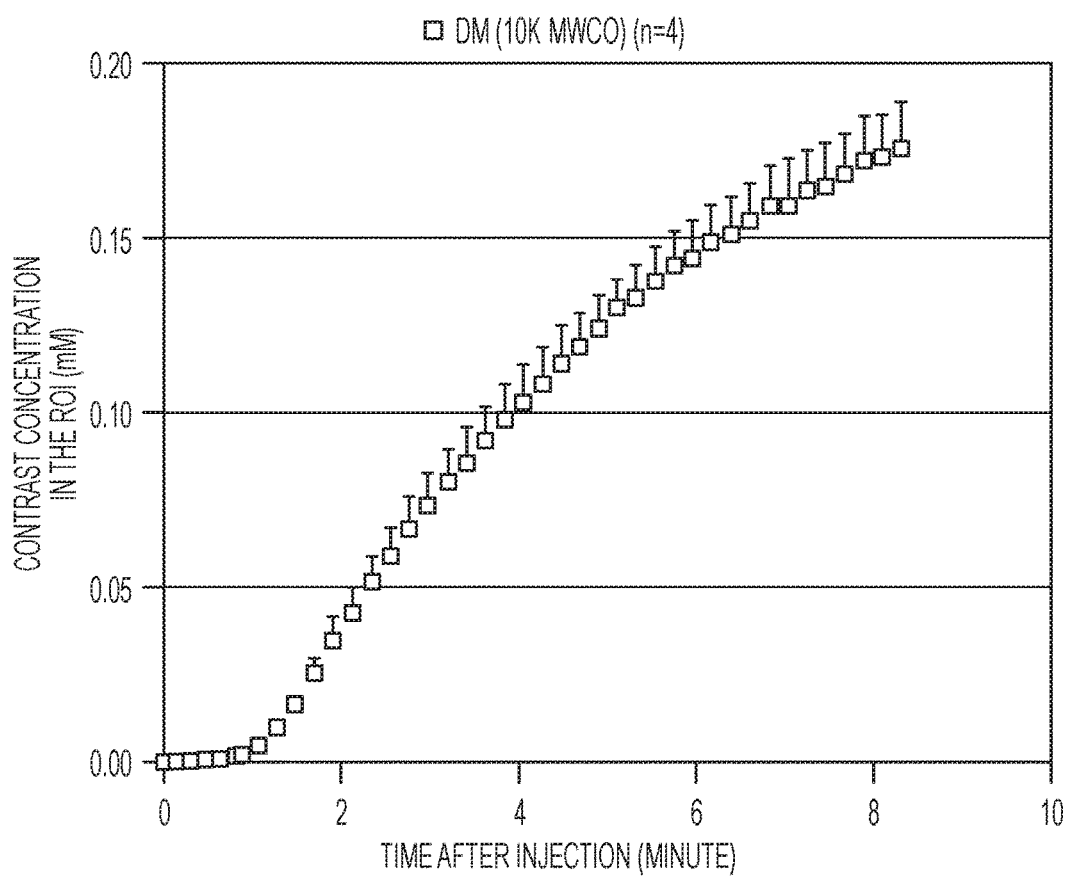
FIG. 5E is a graph showing the contrast concentration change in the Region of Interest (ROI) when commercial dialysis (DM) membranes (n=4) with 10,000 molecular weight cut-off (10K MWCO) were used (mean±SD).

FIGS. 5A-5C show the photographs (top and side views) and schematic of the DCE-MRI phantom, respectively. FIG. 5D shows MR images of the phantom before (baseline) and at 0, 4, and 8.5 minutes after gadoteridol (25 mM) infusion, acquired using a small-animal 9.4 T MR scanner, when the middle and bottom chambers were filled with deionized water. FIG. 5E shows the curve of contrast concentration over time when contrast was infused at 0 minute. Commercial dialysis membranes (n=4) with 10,000 molecular-weight cut-off (10K MWCO) were used. The dynamic change of contrast concentration in the top chamber was difficult to directly measure from DCE-MR images because first, the initial contrast concentration (25 mM) was too high, and second, severe partial volume effect can occur in lower resolution clinical MR images. Instead, the contrast concentration in the top chamber can be calculated using the equation, $C_{TC}(t)=C_0-(C_{MC}(t)\times 10)$, where $C_{TC}(t)$ and $C_{MC}(t)$ are contrast concentrations in the top and middle chambers, respectively, and $C_0$ is the initial contrast concentration infused to the top chamber, since the volume of the middle chamber was designed to be exactly 10 times larger than that of the top chamber. When Tofts model (TM) was used (1), $K^{trans}$ values of the membrane were 0.0042±0.0005 $min^{-1}$ (mean±SD) (coefficient of variance (COV): 12%).

Figure 6C:
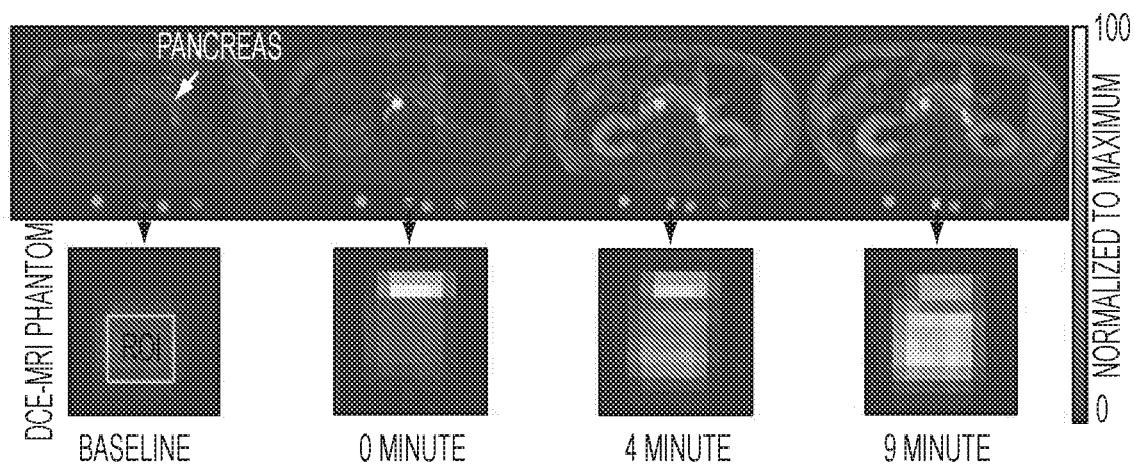
FIG. 6C includes MR images before (baseline) or at 0, 4, and 9 minutes after contrast injection to both a volunteer (0.1 mmol/kg) and an imaging phantom (25 mM).
Figure 6D:
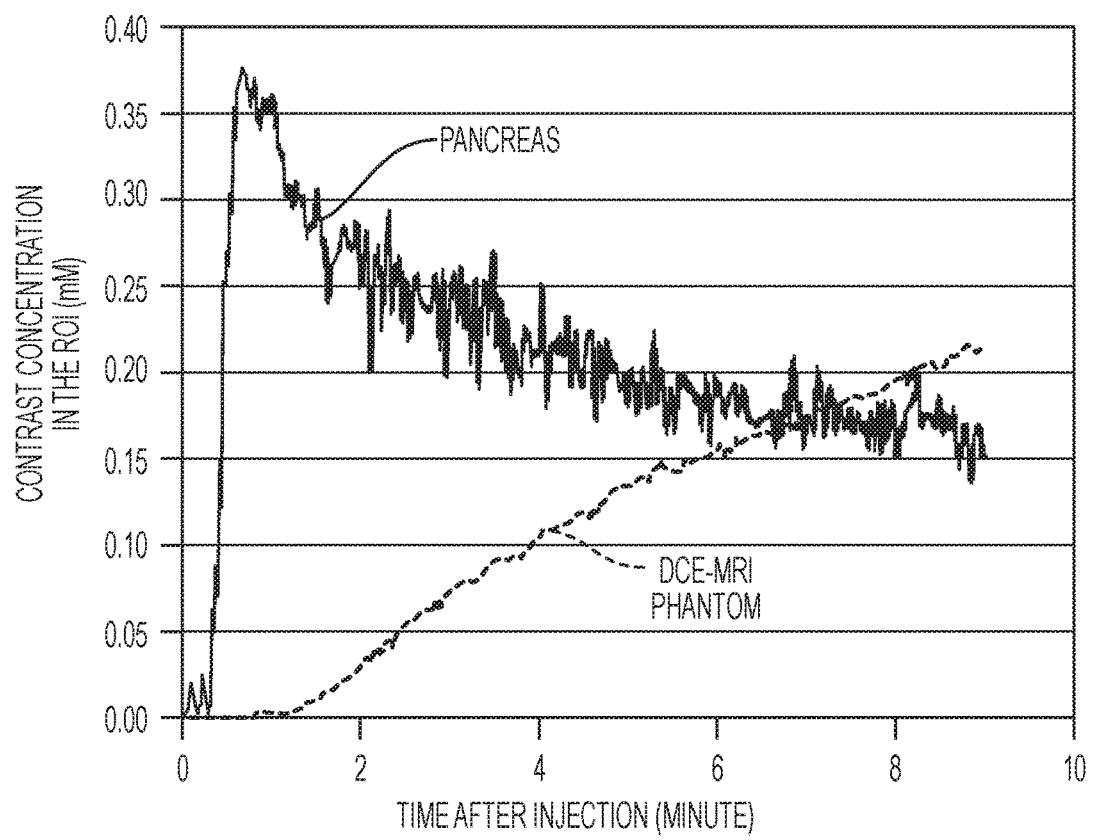
FIG. 6D is a graph showing the change of contrast concentration in the regions of pancreas and the DCE-MRI phantom (ROI).

FIG. 6A shows the DCE-MRI phantom together with three cylindrical phantoms having 0.1, 0.05, and 0.025 mM of gadoteridol, respectively; the bottom chamber of the DCE-MRI phantom was empty. This was located under a volunteer, as shown in FIG. 6B, and imaged using an abdominal DCE-MRI protocol developed for a 3 T MR scanner. Voxel size of each 3D image was 1.56×1.56×2.5 mm, the field of view was 400×400×25 mm (10 image slices), and temporal resolution was 2.4 seconds. Baseline images were acquired for 30 seconds, and MR contrast (gadoteridol) was infused to the volunteer (0.1 mmol/kg) and DCE-MRI phantom (25 mM) simultaneously. 3D images were acquired continuously for 9 minutes. FIG. 6C shows images of the volunteer (at expiration breathing phase) and phantoms before (baseline) and at 0, 4, and 9 minutes after contrast infusion. The pancreas is indicated with a white arrow, and the images of DCE-MRI phantom are zoomed in. FIG. 6D shows the change of contrast concentration (mM) in the regions of pancreas and DCE-MRI phantom (rectangle in FIG. 6C). The volunteer was shallow breathing, and no post-image processing techniques such as motion correction, noise reduction, and artifact compensation were applied. A commercial dialysis membrane (10K MWCO) was used for the imaging phantom construction. $K^{trans}$ values of this membrane were 0.0043 $min^{-1}$, when Tofts model (TM) was used, and this value is 3% different from the mean values measured at the 9.4 T small-animal MR scanner (shown in FIG. 5E). See Tofts P S, Kermode A G. Measurement of the blood-brain barrier permeability and leakage space using dynamic MR imaging. 1. Fundamental concepts. Magnetic resonance in medicine. 1991; 17(2):357-67.

Example Two

Figure 7A:
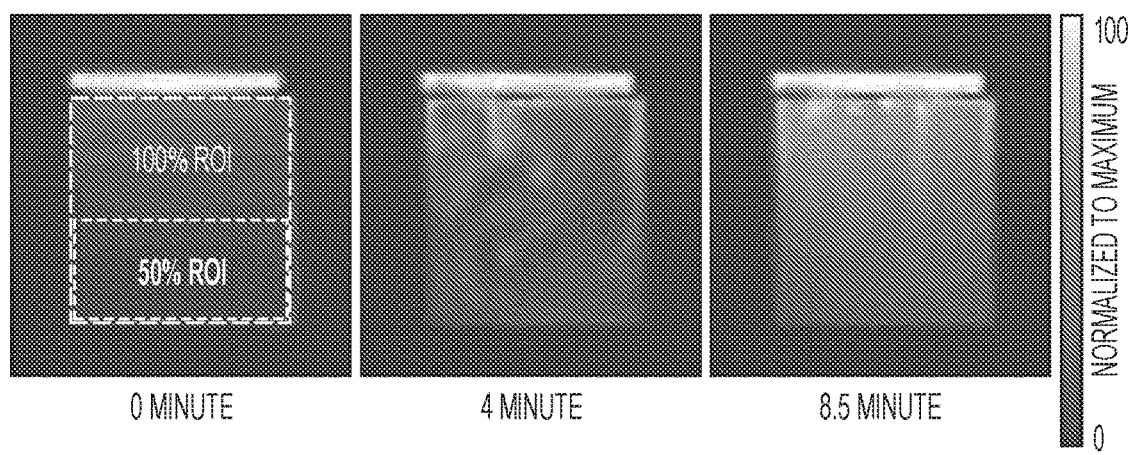
FIG. 7A shows MR images at 0, 4, and 8.5 minutes after contrast infusion, when a Spectra dialysis membrane (12-14K MWCO) was used as disclosed herein.

Among a few commercially available semi-permeable membranes, Spectra/Por2 dialysis membrane (12-14K MWCO) (Spectrum Laboratories Inc.; Rancho Dominguez, Calif.) yielded the highest reproducibility of the perfusion data. FIG. 7A shows the MR images of the perfusion phantom at 0, 4, and 8.5 minutes after contrast infusion (25 mM), when this membrane was used. The coefficient of variance (COV) in calculating $K^{trans}$ value was 4.1% (n=4). When the ROI was reduced to the bottom half (indicated by a 50% ROI rectangle), the mean contrast concentration increased about 20%, because the lower part of the chamber had the higher contrast concentration due to gravity. But, nonetheless, the COV in $K^{trans}$ calculation was still less than 7%.

Figure 7B:
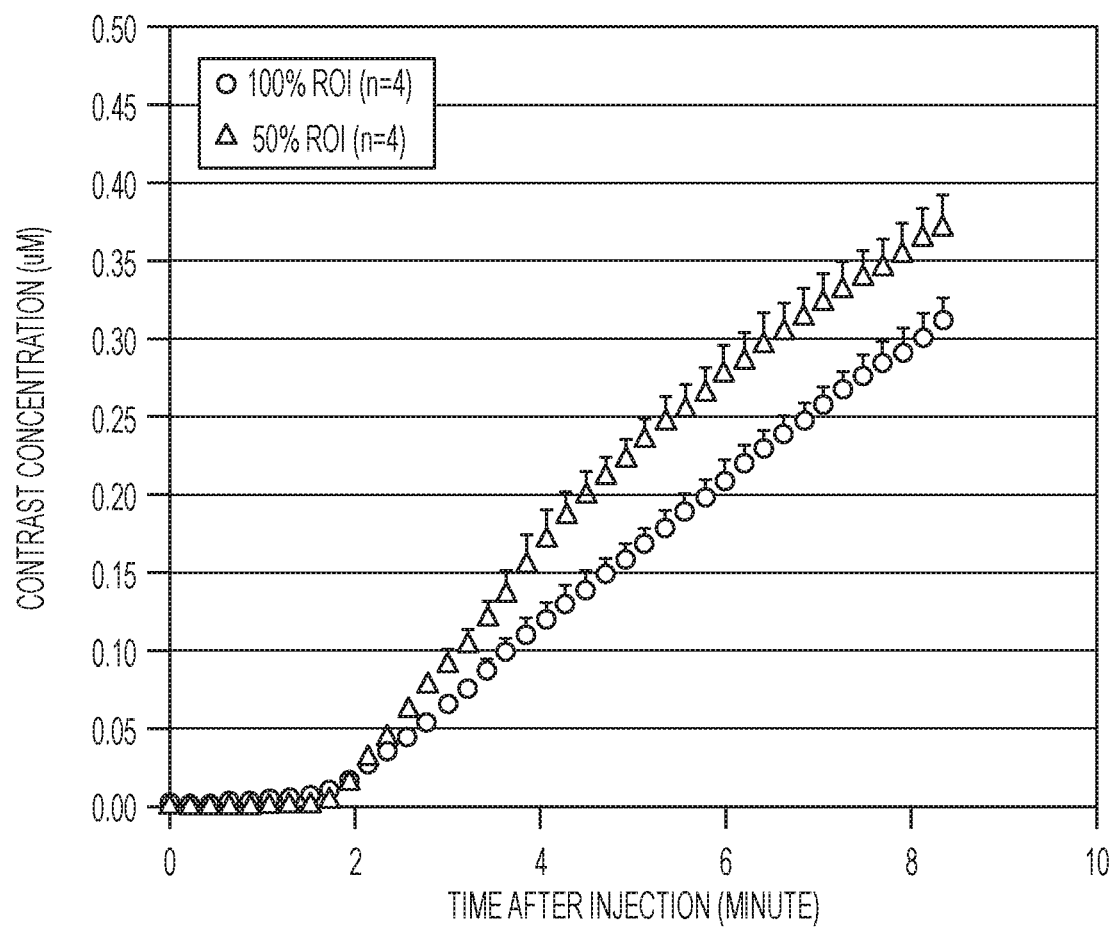
FIG. 7B is a graph showing contrast enhancement curves (mean±SD) in the entire ROI and the bottom half ROI (n=4).

FIG. 7B presents the contrast enhancement curves when the entire ROI (labeled with "100% ROI") or the bottom half ROI (labeled with 50% ROI) was used. The variation of the mean contrast concentration was less than 10% in either ROI over the monitoring time period. These data indicated that multiple contrast enhancement curves may be retrieved from one perfusion phantom as disclosed herein in reasonably high accuracy.

Figure 8B:
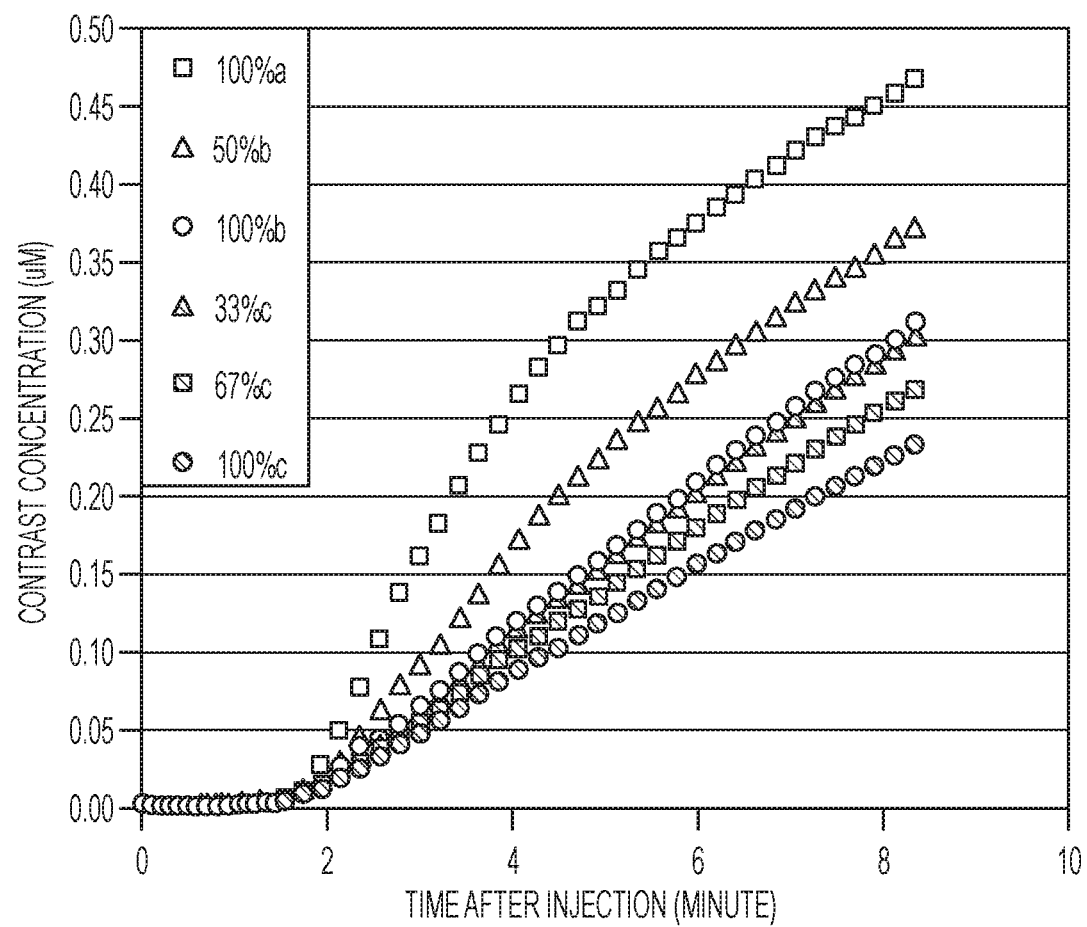
FIG. 8B is a simulated contrast enhancement curve (mM) of the six ROIs in FIG. 8A.

FIG. 8A shows a schematic of a phantom package comprising three perfusion assemblies (a, b, c) and six static chambers. The perfusion assemblies had different chamber sizes (0.75 cm, 1 cm, 1.5 cm). Using the phantom package, contrast-enhancement curves can be retrieved from six different regions of interest (ROIs) 36. The contrast-enhancement curve in the upper region typically presents higher variation, so will not be used. The size of the smallest ROI (50 $mm^2$) is about 20 times larger than the pixel size (2.43 $mm^2$), so partial volume effect should not be a concern. FIG. 8B shows simulated contrast enhancement curves from the six ROIs, when contrast (25 mM) is infused at 0 minute. Assuming the COV in $K^{trans}$ quantification from each curve is less than 7%, the accuracy in $K^{trans}$ calculation of a human tissue using six curves can be higher than 97%. Also, various phantom values can allow compensating offset, scaling, and even non-linear errors.

Six static (fixed concentration, non-diffusion) chambers can be used to compensate for variation in quantitating contrast concentration of a tissue. Each MR scanner can provide unique pulse sequences and reconstruction schemes, which result in variation in quantitating T1 values, contrast concentration, and, consequently, tissue perfusion parameters. The perfusion phantoms can also compensate for this variation because their mean contrast-enhancement curves are consistent over time within 10% error (FIG. 8B). However, since the perfusion phantoms can have operational errors such as incorrect preparation of contrast concentration for infusion, static phantoms with known contrast concentrations can be necessary to confirm the measurement. The correlation coefficient between the real contrast concentrations and the measured ones was higher than 0.95, when three static chambers (0.5-2.0 mM) were used at a clinical 3 T MR scanner. So six static chambers allowed calculating the contrast concentration of a target tissue in higher than 98% accuracy.

A proper thermal insulation method will be determined for the phantoms disclosed herein. The phantom package can be located under a patient as demonstrated in FIG. 6B, thus patient body temperature can be transferred to the patient, changing T1 values and the contrast diffusion coefficient. Polystyrene was tested (R-value: 5.5) for thermal insulation. The thickness of polystyrene to allow heat transfer less than 1° C. (about 1% error in T1 measurement) after contacting human body (35° C.) for an hour was determined. Thermal insulation material can be covered by a non-metallic frame to support patient weight, and then by cushion (~1 cm thickness) to reduce patient discomfort. The frame and the cushion can serve as additional thermal insulators. A typical MR bore size is about 40 cm; thus, the height (vertical dimension) of the phantoms disclosed herein can be about 5 cm. The phantoms were located relatively at the periphery of the field of view (FOV), but no difference was observed according to the phantom location within FOV in the aspect of the signal-to-noise ratio (SNR).

Exemplary Aspects

In view of the described devices, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An imaging phantom comprising: a housing; and a dynamic perfusion assembly positioned within the housing and configured to permit the flow of at least one contrast agent into a non-contrast solution at a desired rate, wherein the dynamic perfusion assembly comprises: a first chamber configured to receive at least one contrast agent; and a second chamber configured to receive a non-contrast solution, and wherein the second chamber is configured to receive the at least one contrast agent from the first chamber at the desired rate.

Aspect 2: The imaging phantom of aspect 1, wherein the dynamic perfusion assembly is configured to maintain a substantially constant temperature within the first and second chambers.

Aspect 3: The imaging phantom of aspect 1 or aspect 2, further comprising a static chamber positioned within the housing and configured to receive a liquid mixture of a non-contrast solution and at least one contrast agent, wherein the static chamber is configured to maintain a concentration of the at least one contrast agent within the liquid mixture.

Aspect 4: The imaging phantom of anyone of the preceding aspects, wherein the dynamic perfusion assembly further comprises a semi-permeable membrane positioned between and in fluid communication with the first chamber and the second chamber.

Aspect 5: The imaging phantom of aspect 4, wherein the first and second chambers are spaced apart relative to a perfusion axis, wherein the semi-permeable membrane is substantially planar, and wherein the semi-permeable membrane is oriented substantially perpendicularly to the perfusion axis.

Aspect 6: The imaging phantom of aspect 5, further comprising an insert that is secured between the first and second chambers of the dynamic perfusion assembly, wherein the insert is configured to support the semi-permeable membrane in a substantially perpendicular orientation relative to the perfusion axis.

Aspect 7: The imaging phantom of any one of aspects 4-6, wherein the desired rate is a substantially constant rate during an initial perfusion period of less than or equal to five minutes.

Aspect 8: The imaging phantom of any one of aspects 4-7, wherein the first and second chambers of the dynamic perfusion assembly have respective volumes, and wherein the volume of the second chamber has a desired ratio relative to the volume of the first chamber.

Aspect 9: The imaging phantom of aspect 8, wherein the semi-permeable membrane is configured to maintain the respective volumes of the first and second chambers.

Aspect 10: The imaging phantom of aspect 8 or aspect 9, wherein the imaging phantom is configured for positioning within a bore of an MRI scanner.

Aspect 11: The imaging phantom of aspect 10, wherein the first chamber of the dynamic perfusion assembly is configured to receive at least one MRI contrast agent, and wherein the second chamber is configured to receive the at least one MRI contrast agent from the first chamber at the desired rate.

Aspect 12: The imaging phantom of any one of aspects 3-7, wherein the imaging phantom is configured for positioning within a bore of an MRI scanner.

Aspect 13: The imaging phantom of aspect 12, wherein the first chamber of the dynamic perfusion assembly is configured to receive at least one MRI contrast agent, wherein the second chamber is configured to receive the at least one MRI contrast agent from the first chamber at the desired rate, wherein the static chamber is configured to receive a liquid mixture of a non-contrast solution and at least one MRI contrast agent, and wherein the static chamber is configured to maintain a concentration of the at least one MRI contrast agent within the liquid mixture.

Aspect 14: An imaging system comprising: an imaging device having a bore configured to receive at least a portion of a subject; and an imaging phantom configured for positioning within the bore of the imaging device and comprising: a housing; and a dynamic perfusion assembly positioned within the housing and configured to permit the flow of at least one contrast agent into a non-contrast solution at a desired rate, wherein the dynamic perfusion assembly comprises: a first chamber configured to receive at least one contrast agent; and a second chamber configured to receive a non-contrast solution, and wherein the second chamber is configured to receive the at least one contrast agent from the first chamber at the desired rate.

Aspect 15: The imaging system of aspect 14, wherein the dynamic perfusion assembly is configured to maintain a substantially constant temperature within the first and second chambers.

Aspect 16: The imaging system of aspect 14 or aspect 15, wherein the imaging phantom further comprises a static chamber positioned within the housing and configured to receive a liquid mixture of a non-contrast solution and at least one contrast agent, and wherein the static chamber is configured to maintain a concentration of the at least one contrast agent within the liquid mixture.

Aspect 17: The imaging system of any one of aspects 14-16, wherein the dynamic perfusion assembly further comprises a semi-permeable membrane positioned between and in fluid communication with the first chamber and the second chamber.

Aspect 18: The imaging system of aspect 17, wherein the first and second chambers of the imaging phantom are spaced apart relative to a perfusion axis, wherein the semi-permeable membrane is substantially planar, and wherein the semi-permeable membrane is oriented substantially perpendicularly to the perfusion axis.

Aspect 19: The imaging system of aspect 18, wherein the imaging phantom further comprises an insert that is secured between the first and second chambers of the dynamic perfusion assembly, wherein the insert is configured to support the semi-permeable membrane in a substantially perpendicular orientation relative to the perfusion axis.

Aspect 20: The imaging system of any one of aspects 17-19, wherein the desired rate is a substantially constant rate during an initial perfusion period of less than or equal to five minutes.

Aspect 21: The imaging system of any one of aspects 17-20, wherein the first and second chambers of the dynamic perfusion assembly have respective volumes, and wherein the volume of the second chamber has a desired ratio relative to the volume of the first chamber.

Aspect 22: The imaging system of aspect 21, wherein the semi-permeable membrane is configured to maintain the respective volumes of the first and second chambers.

Aspect 23: The imaging system of aspect 21 or aspect 22, wherein the imaging device is an MRI scanner.

Aspect 24: The imaging system of aspect 23, wherein the first chamber of the dynamic perfusion assembly is configured to receive at least one MRI contrast agent, and wherein the second chamber is configured to receive the at least one MRI contrast agent from the first chamber at the desired rate.

Aspect 25: The imaging system of any one of aspects 16-20, wherein the imaging device is an MRI scanner.

Aspect 26: The imaging system of aspect 25, wherein the first chamber of the dynamic perfusion assembly is configured to receive at least one MRI contrast agent, wherein the second chamber is configured to receive the at least one MRI contrast agent from the first chamber at the desired rate, wherein the static chamber is configured to receive a liquid mixture of a non-contrast solution and at least one MRI contrast agent, and wherein the static chamber is configured to maintain a concentration of the at least one MRI contrast agent within the liquid mixture.

Aspect 27: An imaging method comprising: positioning an imaging phantom within a bore of an imaging device, the imaging phantom comprising: a housing; and a dynamic perfusion assembly positioned within the housing, wherein the dynamic perfusion assembly permits the flow of at least one contrast agent into a non-contrast solution at a desired rate, and wherein the dynamic perfusion assembly comprises: a first chamber that receives at least one contrast agent; and a second chamber that receives a non-contrast solution, wherein the second chamber receives the at least one contrast agent from the first chamber at the desired rate.

Aspect 28: The imaging method of aspect 27, wherein the dynamic perfusion assembly maintains a substantially constant temperature within the first and second chambers.

Aspect 29: The imaging method of aspect 27 or aspect 28, wherein the imaging phantom further comprises a static chamber positioned within the housing, wherein the static chamber receives a liquid mixture of a non-contrast solution and at least one contrast agent, and wherein the static chamber maintains a concentration of the at least one contrast agent within the liquid mixture.

Aspect 30: The imaging method of any one of aspects 27-29, wherein the dynamic perfusion assembly further comprises a semi-permeable membrane positioned between and in fluid communication with the first chamber and the second chamber.

Aspect 31: The imaging method of aspect 30, wherein the first and second chambers of the imaging phantom are spaced apart relative to a perfusion axis, wherein the semi-permeable membrane is substantially planar, and wherein the semi-permeable membrane is oriented substantially perpendicularly to the perfusion axis.

Aspect 32: The imaging method of aspect 31, wherein the imaging phantom further comprises an insert that is secured between the first and second chambers of the dynamic perfusion assembly, and wherein the insert supports the semi-permeable membrane in a substantially perpendicular orientation relative to the perfusion axis.

Aspect 33: The imaging method of any one of aspects 30-32, wherein the desired rate is a substantially constant rate during an initial perfusion period of less than or equal to five minutes.

Aspect 34: The imaging method of any one of aspects 30-33, wherein the first and second chambers of the dynamic perfusion assembly have respective volumes, and wherein the volume of the second chamber has a desired ratio relative to the volume of the first chamber.

Aspect 35: The imaging method of aspect 34, wherein the semi-permeable membrane maintains the respective volumes of the first and second chambers.

Aspect 36: The imaging method of aspect 34 or aspect 35, wherein the imaging device is an MRI scanner.

Aspect 37: The imaging method of aspect 36, wherein the first chamber of the dynamic perfusion assembly receives at least one MRI contrast agent, and wherein the second chamber receives the at least one MRI contrast agent from the first chamber at the desired rate.

Aspect 38: The imaging method of any one of aspects 29-33, wherein the imaging device is an MRI scanner.

Aspect 39: The imaging method of aspect 38, wherein the first chamber of the dynamic perfusion assembly receives at least one MRI contrast agent, wherein the second chamber receives the at least one MRI contrast agent from the first chamber at the desired rate, wherein the static chamber receives a liquid mixture of a non-contrast solution and at least one MRI contrast agent, and wherein the static chamber maintains a concentration of the at least one MRI contrast agent within the liquid mixture.

Aspect 40: The imaging method of aspect 39, wherein the at least one MRI contrast agent is infused into the first chamber to an initial MRI contrast agent concentration.

Aspect 41: The imaging method of aspect 40, wherein the method further comprises determining, through a processor, a current MRI contrast agent concentration within the first chamber during operation of the imaging device.

Aspect 42: The imaging method of aspect 41, wherein the current MRI contrast agent concentration within the first chamber is determined using the equation:

$$C_{FC}(t) = C_0 - (C_{SC}(t) \times R), \text{ where:}$$

$C_{FC}(t)$ is the current MRI contrast concentration within the first chamber;

$C_0$ is the initial MRI contrast concentration within the first chamber;

$C_{SC}(t)$ is the current MRI contrast concentration within the second chamber; and R is the ratio of the volume of the second chamber to the volume of the first chamber.

Aspect 43: The imaging method of any one of aspects 36-37, wherein during operation of the MRI scanner, the imaging phantom and a subject are both positioned within the bore of the MRI scanner, and wherein the MRI scanner images both the imaging phantom and the subject.

Aspect 44: The imaging method of any one of aspects 38-42, wherein during operation of the MRI scanner, the imaging phantom and a subject are both positioned within the bore of the MRI scanner, and wherein the MRI scanner images both the imaging phantom and the subject.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

What is claimed is:

1. An imaging phantom comprising:
    a housing;
    a dynamic perfusion assembly positioned within the housing and configured to permit the flow of at least one contrast agent into a non-contrast solution at a desired rate, wherein the dynamic perfusion assembly comprises:
        a first chamber configured to receive at least one contrast agent; and
        a second chamber configured to receive a non-contrast solution, and wherein the second chamber is configured to receive the at least one contrast agent from the first chamber at the desired rate; and
    a static chamber positioned within the housing and configured to receive a liquid mixture of a non-contrast solution and at least one contrast agent, wherein the static chamber is configured to maintain a concentration of the at least one contrast agent within the liquid mixture.

2. The imaging phantom of claim 1, wherein the dynamic perfusion assembly is configured to maintain a substantially constant temperature within the first and second chambers.

3. The imaging phantom of claim 1, wherein the dynamic perfusion assembly further comprises a semi-permeable membrane positioned between and in fluid communication with the first chamber and the second chamber.

4. The imaging phantom of claim 1, wherein the imaging phantom is configured for positioning within a bore of an MRI scanner.

5. The imaging phantom of claim 4, wherein the first chamber of the dynamic perfusion assembly is configured to receive at least one MRI contrast agent, wherein the second chamber is configured to receive the at least one MRI contrast agent from the first chamber at the desired rate, wherein the static chamber is configured to receive a liquid mixture of a non-contrast solution and at least one MRI contrast agent, and wherein the static chamber is configured to maintain a concentration of the at least one MRI contrast agent within the liquid mixture.

6. An imaging system comprising:
    an imaging device having a bore configured to receive at least a portion of a subject; and
    an imaging phantom configured for positioning within the bore of the imaging device and comprising:
        a housing;
        a dynamic perfusion assembly positioned within the housing and configured to permit the flow of at least one contrast agent into a non-contrast solution at a desired rate, wherein the dynamic perfusion assembly comprises:
            a first chamber configured to receive at least one contrast agent; and
            a second chamber configured to receive a non-contrast solution, and wherein the second chamber is configured to receive the at least one contrast agent from the first chamber at the desired rate; and
        a static chamber positioned within the housing and configured to receive a liquid mixture of a non-contrast solution and at least one contrast agent, and wherein the static chamber is configured to maintain a concentration of the at least one contrast agent within the liquid mixture.

7. The imaging system of claim 6, wherein the dynamic perfusion assembly is configured to maintain a substantially constant temperature within the first and second chambers.

8. The imaging system of claim 6, wherein the imaging device is an MRI scanner.

9. The imaging system of claim 8, wherein the first chamber of the dynamic perfusion assembly is configured to receive at least one MRI contrast agent, wherein the second chamber is configured to receive the at least one MRI contrast agent from the first chamber at the desired rate, wherein the static chamber is configured to receive a liquid mixture of a non-contrast solution and at least one MRI contrast agent, and wherein the static chamber is configured to maintain a concentration of the at least one MRI contrast agent within the liquid mixture.

10. An imaging method comprising:
positioning an imaging phantom within a bore of an imaging device, the imaging phantom comprising:
  a housing;
  a dynamic perfusion assembly positioned within the housing, wherein the dynamic perfusion assembly permits the flow of at least one contrast agent into a non-contrast solution at a desired rate, and wherein the dynamic perfusion assembly comprises:
    a first chamber that receives at least one contrast agent; and
    a second chamber that receives a non-contrast solution, wherein the second chamber receives the at least one contrast agent from the first chamber at the desired rate; and
  a static chamber positioned within the housing, wherein the static chamber receives a liquid mixture of a non-contrast solution and at least one contrast agent, and wherein the static chamber maintains a concentration of the at least one contrast agent within the liquid mixture.

11. The imaging method of claim 10, wherein the dynamic perfusion assembly maintains a substantially constant temperature within the first and second chambers.

12. The imaging method of claim 10, wherein the imaging device is an MRI scanner.

13. The imaging method of claim 12, wherein the first chamber of the dynamic perfusion assembly receives at least one MRI contrast agent, wherein the second chamber receives the at least one MRI contrast agent from the first chamber at the desired rate, wherein the static chamber receives a liquid mixture of a non-contrast solution and at least one MRI contrast agent, and wherein the static chamber maintains a concentration of the at least one MRI contrast agent within the liquid mixture.

14. The imaging method of claim 13, wherein the at least one MRI contrast agent is infused into the first chamber to an initial MRI contrast agent concentration.

15. The imaging method of claim 14, wherein the method further comprises determining, through a processor, a current MRI contrast agent concentration within the first chamber during operation of the imaging device.

16. The imaging method of claim 15, wherein the current MRI contrast agent concentration within the first chamber is determined using the equation:

$$C_{FC}(t) = C_0 - (C_{SC}(t) \times R), \text{ where:}$$

$C_{FC}(t)$ is the current MRI contrast concentration within the first chamber;

$C_0$ is the initial MRI contrast concentration within the first chamber;

$C_{SC}(t)$ is the current MRI contrast concentration within the second chamber; and R is the ratio of the volume of the second chamber to the volume of the first chamber.

17. The imaging method of claim 12, wherein during operation of the MRI scanner, the imaging phantom and a subject are both positioned within the bore of the MRI scanner, and wherein the MRI scanner images both the imaging phantom and the subject.

* * * * *